United States Patent
Kagayama et al.

[11] Patent Number: 5,939,427
[45] Date of Patent: Aug. 17, 1999

[54] LOTION FOR FK 506

[75] Inventors: Akira Kagayama, Nara; Sachiyo Tanimoto, Osaka; Saburo Murata, Hyogo; Takehisa Hata, Kyoto, all of Japan

[73] Assignee: Fujisawa Pharmaceutical Co., Ltd., Osaka, Japan

[21] Appl. No.: 09/002,887

[22] Filed: Jan. 5, 1998

Related U.S. Application Data

[63] Continuation of application No. 08/537,948, filed as application No. PCT/JP94/00863, May 30, 1994, abandoned.

[30] Foreign Application Priority Data

Jun. 8, 1993 [JP] Japan ................................. 5-137924

[51] Int. Cl.$^6$ .................................................. A61K 31/44
[52] U.S. Cl. .......................................... 514/291; 514/294
[58] Field of Search .................................. 514/291, 294

[56] References Cited

U.S. PATENT DOCUMENTS 5,260,301  11/1993  Nakanishi et al. ...................... 514/291
5,368,865  11/1994  Asakura et al. ......................... 424/489
5,385,907  1/1995   Asakura et al. ......................... 514/291
5,601,844  2/1997   Kagayama et al. ...................... 424/489

*Primary Examiner*—Theodore J. Criares
*Attorney, Agent, or Firm*—Oblon, Spivak, McClelland, Maier & Neustadt, P.C.

[57] ABSTRACT

A lotion comprising a tricyclic compound, typically 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone,[001b] or a pharmaceutically acceptable salt thereof, a solubilizing and/or absorption-promoting agent, a liquid medium, and optionally an emulsifier and/or a viscosity increasing agent. The lotion is stable, excellent in absorption and has less irritation against the skin and sustained release. Also, the lotion is effective for the treatment and/or prophylaxis of inflammatory and hyperproliferative skin diseases and cutaneous manifestations of immunologically-mediated illnesses.

13 Claims, No Drawings

LOTION FOR FK 506

This application is a continuation of application Ser. No. 08/537,948 filed on Nov. 21, 1995, now abandoned, which was filed as International Application No. PCT/JP94/00863 filed May 30, 1994.

FIELD OF THE INVENTION

The present invention relates to a lotion comprising a tricyclic compound represented by the formula (I) or a pharmaceutically acceptable salt thereof which is stable and excellent in absorption, and can be sustainedly released. The lotion is useful for the treatment and prophylaxis of inflammatory and hyperproliferative skin diseases and cutaneous manifestations of immunologically-mediated illnesses.

TECHNICAL BACKGROUND AND PRIOR ART

A tricyclic compound (I) and a pharmaceutically acceptable salt thereof used in the present invention have been known to possess excellent pharmacological activities such as an immunosuppressive activity and an antimicrobial activity, thereby being useful for treating and preventing rejection against organ-transplantation or tissue-transplantation, graft versus host reaction, various autoimmune diseases and infectious diseases (Japanese Laid-Open Patent Application No. 61(1986)-148181, EP-A-0323042).

Particularly, compounds referred as FR900506(=FK 506 substance), FR900520, FR900523 and FR900525 which belong to the tricyclic compound (I) are produced from genus Streptomyces, in particular, Streptomyces tsukubaensis No. 9993 (Depositary Authority: 1–3, Higashi 1 chome, Yatabe-machi, Tsukuba-gun, Ibaraki-ken, Japan, Fermentation Research Institute Agency of Industrial Science and Technology, Ministry of International Trade and Industry; Date of the Deposit: 5 Oct. 1984; Accession Number: FERM BP-927) or Streptomyces hygroscopicus Subsp. yakushimaensis No. 7238 (Depositary Authority: 1–3, Higashi 1 chome, Yatabe-machi, Tsukuba-gun, Ibaraki-ken, Japan, Fermentation Research Institute Agency of Industrial Science and Technology, Ministry of International Trade and Industry; Date of the Deposit: Jan. 12, 1985; Accession Number: FERM BP-928). In particular, FK 506 substance represented by the following structural formula is a typical compound.

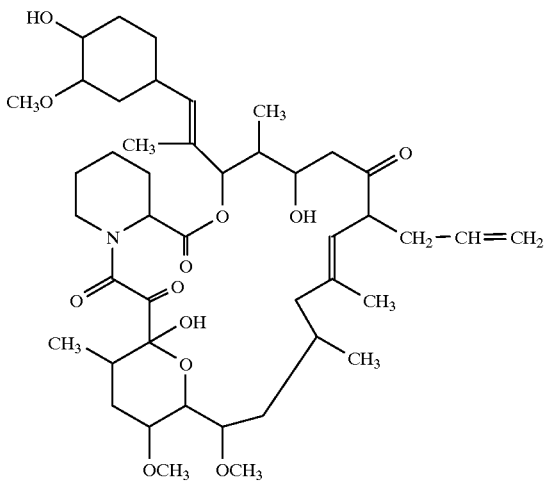

Chemical name: 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

It is known that FK 506 substance described above has excellent immunosuppressive activities and is useful for treating and preventing rejection against organ-transplantation and eye diseases.

The Japanese Laid-Open Patent Application No. 1(1989)-157913 teaches that FK 506 substance dissolved in ethanol is effective against inflammatory inhibition and FK 506 substance can be formulated in the form of a lotion, gel and cream. However, there is no disclosure in the publication about specific preparations of the lotion, gel and cream.

Also, Japanese Laid-Open Patent Application No. 5(1993)-17481 discloses ointment comprising a tricyclic compound (I) or a pharmaceutically acceptable salt thereof, a solubilizing and/or absorption-promoting agent in an amount at least sufficient to dissolve the tricyclic compound or its salt, and an ointment base.

Ointment or the like has been mainly used for treating skin disease. However, various types of preparation are demanded depending on the part to be applied. For example, in case of application to the head skin, it is preferred that less amount of the formulation remains after the application.

DISCLOSURE OF THE INVENTION

The present inventors have made studies about a lotion comprising a compound represented by the formula (I) including FK 506 substance, and found out a preparation which is excellent in stability and absorption through skin and can be sustainedly released.

The present invention provides a lotion comprising a tricyclic compound represented by the formula (I):

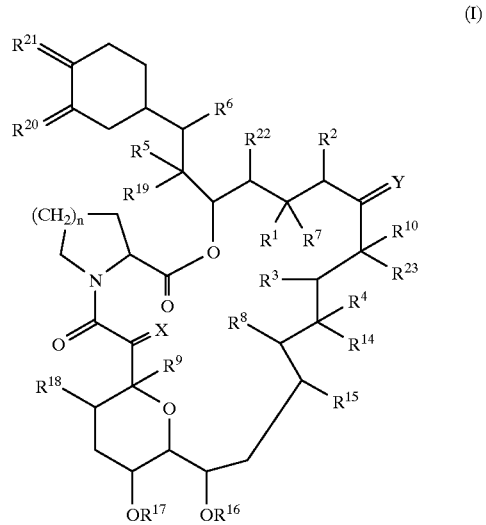

(I)

wherein each of adjacent pairs of $R^1$ and $R^2$, $R^3$ and $R^4$ or $R^5$ and $R^6$ independently (a) is two adjacent hydrogen atoms, or
(b) may form another bond formed between the carbon atoms to which they are attached, and further, $R^2$ may be an alkyl group;

$R^7$ is a hydrogen atom, a hydroxy group, a protected hydroxy group or an alkoxy group, or an oxo group together with $R^1$; each of $R^8$ and $R^9$ is independently a hydrogen atom or a hydroxy group;

$R^{10}$ is a hydrogen atom, an alkyl group, an alkyl group substituted by one or more hydroxy groups, an alkenyl group, an alkenyl group substituted by one or more hydroxy groups or an alkyl group substituted by an oxo group;

X is an oxo group, (a hydrogen atom and a hydroxy group),(a hydrogen atom and a hydrogen atom), or a group represented by the formula —CH$_2$O—;

Y is an oxo group, (a hydrogen atom and a hydroxy group), (a hydrogen atom and a hydrogen atom), or a group represented by the formula N—NR$^{11}$R$^{12}$ or N—OR$^{13}$;

each of R$^{11}$ and R$^{12}$ is independently a hydrogen atom, an alkyl group, an aryl group or a tosyl group;

each of R$^{13}$, R$^{14}$, R$^{15}$, R$^{16}$, R$^{17}$, R$^{18}$, R$^{19}$, R$^{22}$ and R$^{23}$ is independently a hydrogen atom or an alkyl group;

each of R$^{20}$ and R$^{21}$ is independently an oxo group or (R$^{20}$a and a hydrogen atom) or (R$^{21}$a and a hydrogen atom) in which each of R$^{20}$a and R$^{21}$a is independently a hydroxy group, an alkoxy group or a group represented by the formula —OCH$_2$OCH$_2$CH$_2$OCH$_3$, or R$^{21}$a is a protected hydroxy group, or R$^{20}$a and R$^{21}$a may together represent an oxygen atom in an epoxide ring;

n is an integer of 1, 2 or 3; and in addition to the above definitions, Y, R$^{10}$ and R$^{23}$, together with the carbon atoms to which they are attached, may represent a saturated or unsaturated 5- or 6- membered nitrogen, sulfur and/or oxygen containing heterocyclic ring optionally substituted by one or more groups selected from the group consisting of an alkyl, a hydroxy, an alkyl substituted by one or more hydroxy groups, an alkoxy, a benzyl, and a group of the formula —CH$_2$Se(C$_6$H$_5$);

or a pharmaceutically acceptable salt thereof, a solubilizing and/or absorption-promoting agent, a liquid medium, and optionally an emulsifier and/or a viscosity increasing agent.

Hereinafter, various terms which are included in the scope of the present invention will be defined.

Each definition in the formula (I) will be detailed as follows.

The term "lower" means, unless otherwise indicated, a group having 1 to 6 carbon atoms. Preferable examples of the "alkyl groups" include a straight or branched chain aliphatic hydrocarbon residue, for example, a lower alkyl group such as methyl, ethyl, propyl, isopropyl, butyl, isobutyl, pentyl, neopentyl and hexyl. Preferable examples of the "alkenyl groups" include a straight or branched chain aliphatic hydrocarbon residue having one double-bond, for example, a lower alkenyl group such as vinyl, propenyl (e.g., allyl group), butenyl, methylpropenyl, pentenyl and hexenyl. Preferable examples of the "aryl groups" include phenyl, tolyl, xylyl, cumenyl, mesityl and naphthyl.

Preferable protective groups in the "protected hydroxy groups" are 1-(lower alkylthio)(lower)alkyl group such as a lower alkylthiomethyl group (e.g., methylthiomethyl, ethylthiomethyl, propylthiomethyl, isopropylthiomethyl, butylthiomethyl, isobutylthiomethyl, hexylthiomethyl, etc.), more preferably C$_{1-4}$ alkylthiomethyl group, most preferably methylthiomethyl group; trisubstituted silyl group such as a tri(lower)alkylsilyl (e.g., trimethylsilyl, triethylsilyl, tributylsilyl, tert-butyldimethylsilyl, tri-tert-butylsilyl, etc.) or lower alkyl-diarylsilyl (e.g., methyldiphenylsilyl, ethyldiphenylsilyl, propyldiphenylsilyl, tert-butyldiphenylsilyl, etc.), more preferably tri(C$_{1-4}$)alkylsilyl group and C$_{1-4}$ alkyldiphenylsilyl group, most preferably tert-butyl-dimethylsilyl group and tert-butyldiphenylsilyl group; or an acyl group such as an aliphatic, aromatic acyl group or an aliphatic acyl group substituted by an aromatic group, which are derived from a carboxylic acid, sulfonic acid or carbamic acid.

Examples of the aliphatic acyl groups include a lower alkanoyl group optionally having one or more suitable substituents such as carboxy, e.g., formyl, acetyl, propionyl, butyryl, isobutyryl, valeryl, isovaleryl, pivaloyl, hexanoyl, carboxyacetyl, carboxypropionyl, carboxybutyryl, carbocyhecanoyl, etc.; a cyclo(lower)alkoxy(lower)alkanoyl group optionally having one or more suitable substituents such as lower alkyl, e.g., cyclopropyloxyacetyl, cyclobutyloxypropionyl, cycloheptyloxybutyryl, menthyloxyacetyl, menthyloxypropionyl, menthyloxybutyryl, menthyloxypentanoyl, menthyloxyhexanoyl, etc.; a camphorsulfonyl group; or a lower alkylcarbamoyl group having one or more suitable substituents such as carboxy or protected carboxy, for example, carboxy(lower)alkylcarbamoyl group (e.g., carboxymethylcarbamoyl, carboxyethylcarbamoyl, carboxypropylcarbamoyl, carboxybutylcarbamoyl, carboxypentylcarbamoyl, carboxyhexylcarbamoyl, etc.), tri(lower)alkylsilyl(lower)alkoxycarbonyl(lower)alkylcarbamoyl group (e.g., trimethylsilylmethoxycarbonylethylcarbamoyl, trimethylsilylethoxycarbonylpropylcarbamoyl, triethylsilylethoxycarbonylpropylcarbamoyl, tert-butyldimethylsilylethoxycarbonylpropylcarbamoyl, trimethylsilylpropoxycarbonylbutylcarbamoyl, etc.) and so on.

Examples of the aromatic acyl groups include an aroyl group optionally having one or more suitable substituents such as nitro, e.g., benzoyl, toluoyl, xyloyl, naphthoyl, nitrobenzoyl, dinitrobenzoyl, nitronaphthoyl etc.; and an arenesulfonyl group optionally having one or more suitable substituents such as halogen, e.g., benzenesulfonyl, toluenesulfonyl, xylenesulfonyl, naphthalenesulfonyl, fluorobenzenesulfonyl, chlorobenzenesulfonyl, bromobenzenesulfonyl, iodobenzenesulfonyl, etc.

Examples of the aliphatic acyl groups substituted by an aromatic group include ar(lower)alkanoyl group optionally having one or more suitable substituents such as lower alkoxy or trihalo(lower)alkyl, e.g., phenylacetyl, phenylpropionyl, phenylbutyryl, 2-trifluoromethyl-2-methoxy-2-phenylacetyl, 2-ethyl-2-trifluoromethyl-2-phenylacetyl, 2-trifluoromethyl-2-propoxy-2-phenylacetyl, etc.

More preferable acyl groups among the aforesaid acyl groups are C$_{1-4}$ alkanoyl group optionally having carboxy, cyclo(C$_{5-6}$)alkoxy(C$_{1-4}$)alkanoyl group having two (C$_{1-4}$) alkyls at the cycloalkyl moiety, camphorsulfonyl group, carboxy(C$_{1-4}$)alkylcarbamoyl group, tri(C$_{1-4}$)alkylsilyl(C$_{1-4}$)alkoxycarbonyl(C$_{1-4}$)alkylcarbamoyl group, benzoyl group optionally having one or two nitro groups, benzenesulfonyl group having halogen or phenyl(C$_{1-4}$)alkanoyl group having C$_{1-4}$ alkoxy and trihalo(C$_{1-4}$)alkyl group. Among these, the most preferable ones are acetyl, carboxypropionyl, menthyloxyacetyl, camphorsulfonyl, benzoyl, nitrobenzoyl, dinitrobenzoyl, iodobenzenesulfonyl and 2-trifluoro-methyl-2-methoxy-2-phenylacetyl.

Preferable examples of the "5- or 6-membered nitrogen, sulfur and/or oxygen containing heterocyclic ring" include a pyrrolyl group and a tetrahydrofuryl group.

The pharmaceutically acceptable salts of the tricyclic compound (I) include conventional non-toxic and pharmaceutically acceptable salts such as the salts with inorganic or organic bases, specifically, an alkali metal salt such as sodium salt and potassium salt, an alkali earth metal salt such as calcium salt and magnesium salt, an ammonium salt and an amine salt such as triethylamine salt and N-benzyl-N-methylamine salt.

With respect to the tricyclic compound (I), it is to be understood that there may be conformers and one or more stereoisomers such as optical and geometrical isomers due to asymmetric carbon atom(s) and double bond(s), and such conformers and isomers are also included within the scope of the present invention.

FK 506 substance is the most preferable compound belonging to the tricyclic compound (I). Other preferable compounds are listed hereinbelow.

1,14-dihydroxy-12-[2-(4-hydroxy-3-methoxycyclohexyl)-1-methylvinyl]-23,25-dimethoxy-13,19,17,21,27-pentamethyl-11,28-dioxa-4-azatricyclo[22.3.1.0$^{4,9}$]octacos-18-ene-2,3,10,16-tetraone, 12-[2-(4-acetoxy-3-methoxycyclohexyl)-1-methylvinyl]-17-allyl-1,14-dihydroxy-23,25-dimethoxy-13,19,21,27-tetramethyl-11,28-dioxa-4-azatricyclo[22.3.1.0$^{4,9}$]octacos-18-ene-2,3,10,16-tetraone, 17-allyl-1,14-dihydroxy-23,25-dimethoxy-13,19,21,27-tetramethyl-12-[2-[4-(3,5-dinitrobenzoyloxy)-3-methoxycyclohexyl]-1-methylvinyl]-11,28-dioxa-4-azatricyclo[22.3.1.0$^{4,9}$]octacos-18-ene-2,3,10,16-tetraone, 17-allyl-12-[2-[4-[(-)-2-trifluoromethyl-2-methoxy-2-phenylacetoxy]-3-methoxycyclohexyl]-1-methylvinyl]-1,14-dihydroxy-23,25-dimethoxy-13,19,21,27-tetramethyl-11,28-dioxa-4-azatricyclo[22.3.1.0$^{4,9}$]octacos-18-ene-2,3,10,16-tetraone, b 17-ethyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$] octacos- 18-ene-2,3,10,16-tetraone, and 17-ethyl-1,14,20-trihydroxy-12-[2-(3,4-dihydroxycyclohexyl)-1-methylvinyl]-23,25-dimethoxy-13,19,21,27-tetramethyl-11,28-dioxa-4-azatricyclo[22.3.1.0$^{4,9}$] octacos-18-ene-2,3,10,16-tetraone.

The tricyclic compound (I) or its pharmaceutically acceptable salt is contained in the lotion in an amount of 0.01 to 10% (W/W), preferably 0.01 to 5% (W/W).

The lotion used in the present invention means a preparation in which the active ingredient (the tricyclic compound (I) or its pharmaceutically acceptable salt) is dissolved or dispersed finely and uniformly in a liquid medium, and which is used for external administration.

Examples of the liquid medium used in the present invention include water, a lower alcohol, a glycol, glycerin and a mixture thereof. Among them, water, the lower alcohol or a mixture thereof is preferable. As the lower alcohol, any lower alcohol may be used as far as it does not decompose the tricyclic compound (I) or its pharmaceutically acceptable salt and does not irritate skin. For example, methanol, ethanol, isopropylalcohol, etc. are used, and, preferably, ethanol is used. As the glycol, ethylene glycol, propylene glycol, butylene glycol and mono lower ethers thereof, etc. can be used. The liquid medium may be used singly or as a mixture thereof. The liquid medium is used suitably in an amount of 5 to 10,000 parts by weight per 1 part by weight of the tricyclic compound (I) or its pharmaceutically acceptable salt.

The solubilizing and/or absorption-promoting agent used in the present invention means an agent which can dissolve the tricyclic compound (I) or its pharmaceutically acceptable salt with a concentration of at least 0.01% (W/W) or more, and further promote the absorption of the tricyclic compound (I) or its pharmaceutically acceptable salt through skin when formulated as a lotion. In other words, the solubilizing and/or absorption-promoting agent affords solubilizing and absorbing abilities to the tricyclic compound (I) or its pharmaceutically acceptable salt. The agent possessing either one of solubilizing and absorbing abilities is also included in the scope of the solubilizing and/or absorption-promoting agents of the present invention.

As the result of various studies on the agents possessing the above two abilities, the followings are listed as the solubilizing and/or absorption-promoting agent:

alkane dicarboxylic esters such as alkane dicarboxylic dialkyl esters (dimethyl adipate, diethyl adipate, diisopropyl adipate, diethyl pimelate, diethyl sebacate, dipropyl sebacate etc.); and higher alkane carboxylic alkyl esters (isopropyl myristate, ethyl myristate, etc.). Among them, diisopropyl adipate, diethyl sebacate and isopropyl myristate are preferable.

The solubilizing and/or absorption-promoting agent is used suitably in an amount of 5 to 5,000 parts by weight, preferably 10 to 1,000 parts by weight, per 1 part by weight of the tricyclic compound (I) or its pharmaceutically acceptable salt. The solubilizing and/or absorption-promoting agent is contained in the lotion preferably in an amount of 1 to 30% (w/w). In the present invention, the solubilizing and/or absorption-promoting agent may be used singly or as a mixture thereof.

Examples of the emulsifiers used in the present invention are an emulsifier which is generally used for dispersing insoluble drugs in an aqueous liquid finely and uniformly and is non-toxic to human bodies, preferably a pharmaceutically acceptable natural emulsifier or synthetic emulsifier.

As the natural emulsifiers, various types of emulsifiers derived from animal or plant may be used. For example, yolk lecithin, soybean lecithin or a hydrogenated substance thereof, phosphatidylcholine, phosphatidylserine, sphingomyelin, gum arabic, gelatin, etc. are included. As the synthetic emulsifiers, surface active agents of cation, anion or nonion type may be used. Among them, nonionic surface active agents are preferred. In view of a long storage, typical examples of the nonionic surface active agents include those of caster oil type, in particular, HCO (polyoxyethylene-hardened caster oil) type is preferable. More prefarably, HCO-60, HCO-50 and HCO-40 are used. In addition to the above examples, polyoxyethylene sorbitan fatty acid ester derivatives such as polysorbate 80, glycerin fatty acid ester derivatives such as glyceryl monocaprylate, polyethylene fatty acid ester derivatives such as polyoxyethylene 40 monostearate, fatty acid mono(or di)glycerides having a medium size chain [for example, fatty acid mono(or di)glycerides having 6 to 12 carbon atoms such as caprylic acid diglyceride, caprylic acid monoglyceride, caproic acid diglyceride, etc.], and polyoxyethylated glycerides such as polyoxyethylated oleic acid glyceride may be used.

The emulsifiers described above are used as a first emulsifier. If necessary, an auxiliary emulsifier may be also used, which is included in the scope of the present invention. Examples of the auxiliary emulsifiers include those generally used as an auxiliary emulsifier and being non-toxic to human bodies. Typical examples include, for example, cholesterol, agar, magnesium hydroxide, methylcellulose, pectin, etc. The first emulsifier and the auxiliary emulsifier can be used singly or as a mixture thereof.

The emulsifier contained in the lotion of the present invention is at least sufficient in an amount with which the solubilizing and/or absorption-promoting agent to be used can be emulsified, specifically, in an amount of 0.1 to 10 parts by weight, preferably, 0.5 to 5 parts by weight, per 1 part by weight of the tricyclic compound (I) or its pharmaceutically acceptable salt.

A lotion which contains a viscosity increasing agent is also included in the present invention. Examples of the viscosity increasing agents used in the present invention include those generally used in the field to add a viscosity to a liquid, and being non-toxic to human bodies. For example, carboxypolymethylene is used.

In the present invention, the viscosity increasing agent is used when the lotion is required to have a high viscosity. The viscosity increasing agent is contained in the lotion of the present invention in an amount of 0.01 to 5% (w/w), which is defined suitably depending on the desired viscosity of the lotion to be used.

According to the present invention, when water, the lower alcohol, or a mixture of water and the lower alcohol is used as a liquid medium, the absorption of the tricyclic compound (I) or its pharmaceutically acceptable salt to the skin is improved.

A preferable lotion of the present invention comprises the tricyclic compound (I) or its pharmaceutically acceptable salt, the solubilizing and/or absorption-promoting agent and the liquid medium. Among them, a more preferable lotion comprises the tricyclic compound (I) or its pharmaceutically acceptable salt, the solubilizing and/or absorption-promoting agent and the lower alcohol. Most preferable lotion comprises the tricyclic compound (I) or its pharmaceutically acceptable salt; isopropyl myristate or diethyl sebacate as the solubilizing and/or absorption-promoting agent; and ethanol as the lower alcohol.

Another preferable lotion comprises the tricyclic compound (I) or its pharmaceutically acceptable salt, the solubilizing and/or absorption-promoting agent, the liquid medium and the emulsifier. Among them, more preferable lotion comprises the tricyclic compound (I) or its pharmaceutically acceptable salt; isopropyl myristate or diethyl sebacate as the solubilizing and/or absorption-promoting agent; water, the lower alcohol, a mixture of water and the lower alcohol (especially a mixture of water and ethanol), or a mixture of water, the lower alcohol and glycerin (especially a mixture of water, ethanol and glycerin) as the liquid medium; and HCO-60, HCO-50 or HCO-40 (especially HCO-60) as the emulsifier.

Another preferable lotion comprises the tricyclic compound (I) or its pharmaceutically acceptable salt, the solubilizing and/or absorption-promoting agent, the liquid medium, the emulsifier and the viscosity increasing agent. Among them, more preferable lotion comprises the tricyclic compound (I) or its pharmaceutically acceptable salt; isopropyl myristate or diethyl sebacate as the solubilizing and/or absorption-promoting agent; a mixture of water and the lower alcohol (especially a mixture of water and ethanol) as the liquid medium; HCO-60, HCO-50 or HCO-40 (especially HCO-60) as the emulsifier; and carboxypolymethylene as the viscosity increasing agent.

In case that the aqueous medium (especially water) is used as the liquid medium, the lotion of the present invention can be preferably produced by formulating the tricyclic compound (I) or its pharmaceutically acceptable salt and the solubilizing and/or absorption-promoting agent in another liquid medium (lower alcohol, glycerin, glycol, etc.) and mixing it with the aqueous medium (especially water) before using. In this case, the emulsifier or the viscosity increasing agent is previously dissolved in the liquid medium in which the emulsifier or the viscosity increasing agent can be dissolved. Alternatively, if the aqueous medium (especially water) is not used as the liquid medium, it can be stored as a single liquid preparation.

The lotion of the present invention may include a stabilizer which can stabilize the tricyclic compound (I) or its pharmaceutically acceptable salt in an aqueous solution. When such a stabilizer is contained, it is not necessary to mix the tricyclic compound (I) or its pharmaceutically acceptable salt and the solubilizing and/or absorption-promoting agent and the like with the aqueous medium (especially water) and shake the mixture before using, and it can be stored as a single liquid preparation.

When needed, the lotion of the present invention may contain other additives which can be used in a lotion such as flavors, colorants, preservatives and absorption-promoting agents such as higher alkene carboxylic acid (e.g., oleic acid), and other drugs which are effective for skin diseases.

The lotion of the present invention can be applied to the affected part of the skin one to four times a day.

If the lotion of the present invention has a low viscosity, it can be contained in a spraying bottle and applied to the affected part of the skin directly by spraying the lotion.

The lotion of the present invention can also be obtained when the compounds disclosed in patent applications such as EP-A-353678, Japanese Patent Application No. 2(1990)-74330, PCT/GB90/01262, EP-A-413532, PCT/JP91/00314, British Patent Applications No. 9012963.6, No. 9014136.7, No. 9014681.2, No. 9014880.0, No. 9014881.8, No. 9015098.8, No. 9016115.9, and No. 9016693.5, EP-A-323865, EP-A-349061, EP-A-358508, EP-A-364031, EP-A-364032, EP-A-378317, EP-A-378320, EP-A-378321, EP-A-388153, EP-A-396399, EP-A-396400, EP-A-399579, EP-A-403242, EP-A-428365, EP-A-356399, GB 2225576 A, EP-A-402931, EP-A-427680, EP-A-445975, EP-A-455427, EP-A-463690, EP-A-464895, EP-A-466365, EP-A-478235, EP-A-480623, EP-A-509753, EP-A-515071, EP-A-520554, EP-A-526934, EP-A-530888, EP-A-532089, and EP-A-532088, WO92/06992, WO92/20688, WO93/04679, WO93/05059, and WO93/04680, U.S. Pat. No. 5149701, German Patent Applications A-4021404, A-4028664, A-4028665, A-4028666, A-4028667, A-4028675, A-4028676, A-4028677, A-4028678, and A-4039587; cyclosporins such as cyclosporin A; and rapamycins such as rapamycin are employed instead of the tricyclic compound (I) or its pharmaceutically acceptable salt.

The present invention will be described hereinbelow with reference to the following Examples, but it is not intended to limit the scope of the invention.

EXAMPLE 1

FK 506 substance as the tricyclic compound (I), IPM-100 as the solubilizing and/or absorption-promoting agent (isopropyl myristate having 99.5% purity manufactured by NIKKO Chem. Co., Ltd.), and ethanol as the liquid medium were used.

To FK 506 substance (100 mg), IPM-100 (1 ml) and ethanol (4 ml) were added and dissolved at a room temperature to prepare a lotion containing 2% of FK 506 substance.

EXAMPLE 2

A lotion containing 2% of FK 506 substance was prepared in the same manner as in Example 1, except that diisopropyl adipate was used instead of IPM-100 as the solubilizing and/or absorption-promoting agent.

EXAMPLE 3

A lotion containing 2% of FK 506 substance was prepared in the same manner as in Example 1, except that diethyl sebacate was used instead of IPM-100 as the solubilizing and/or absorption-promoting agent.

EXAMPLE 4

FK 506 substance as the tricyclic compound (I), diethyl sebacate as the solubilizing and/or absorption-promoting agent, a mixture of water and ethanol as the liquid medium, HCO-60 as the emulsifier, and carbopol (carboxypolymethylene) as the viscosity increasing agent were used to prepare a lotion containing 0.5% of FK 506 substance in accordance with the method described below.

First, 10% FK 506 substance in ethanol solution (0.5 ml) and HCO-60 (0.05 g) were mixed and stirred at a room temperature, followed by adding diethyl sebacate to have a total amount of 2.5 g (Solution A). Next, distilled water was added to 2% carbopol in aqueous solution (0.5 g) to have a total amount of 7.5 g (Solution B). By mixing Solutions A and B, a lotion containing 0.5% of FK 506 substance was prepared.

EXAMPLE 5

A lotion containing 0.5% of FK 506 substance was prepared in the same manner as in Example 4, except that isopropyl myristate was used instead of diethyl sebacate as the solubilizing and/or absorption-promoting agent.

EXAMPLE 6

A lotion containing 0.5% of FK 506 substance was prepared in the same manner as in Example 4, except that diisopropyl adipate was used instead of diethyl sebacate as the solubilizing and/or absorption-promoting agent.

EXAMPLE 7

Each lotion containing cyclosporin A was prepared in the same manner as in Examples 1 to 6, except that cyclosporin A was used instead of the tricyclic compound (I).

EXAMPLE 8

Each lotion containing rapamycin was prepared in the same manner as in Examples 1 to 6, except that rapamycin was used instead of the tricyclic compound (I).

Next, a cutaneous absorption test for the lotions of the present invention is described.

TEST 1 (in vivo cutaneous absorption test)

The lotions obtained in Examples were used for a cutaneous absorption test. Ethanol solution was used as a control.

As test animals, 5 male SD-rats of 7 weeks old were used for each lotion. They were depilated 24 hours before the administration. First, the rats were fixed on the fixed stand at a dorsal position and depilated by hair clippers (produced by Speedic Co.: 2 mm), followed by applying depilatory cream (eva cream, produced by TOKYO TANABE Pharmaceutical Co., Ltd.) to a thickness of 1 to 3 mm so as to cover the hair. In the application, the cream was applied to the roots of the hair. It was allowed to stand 15 to 20 minutes after the application. Then, the applied part was made wet with absorbent cotton moistened with distilled water, followed by washing tenderly with warm water. After that, the water was wiped off with clean cotton or the like and the rats were released from the fixed stand to be free till the next day.

The rats were fixed to the fixed stand again after 24 hours from the depilation. A square frame of 2.5 cm ×4 cm (10 cm$^2$) was marked on the abdominal skin of the rats, avoiding marking on a damaged part. Heavily damaged rats were not used.

Then, the lotions (25 to 100 μl) prepared in Examples were evenly applied by use of an Eppendorf pipet in the marked square frame.

Before the administration, rats were anesthetized with ether and cannulated to femoral artery. Blood (0.25 ml for each) was collected 1, 3, 5, 8 and 24 hours after the administration.

Thus collected blood was subjected to an enzyme immunoassay using peroxidase as an enzyme (for example, according to a method disclosed in Japanese Laid-Open Patent Application No. 1(1989)-92659) to measure a blood concentration of FK 506 substance.

The cutaneous absorption parameter of each lotion was calculated. The results are shown in Table 1. In Table 1, $C_{max}$ is the maximal blood concentration, $T_{max}$ is the time to maximal blood concentration after the application, and $AUC_{0-24}$ is the area under the blood concentration-time curve from 0 to 24 hours after the application.

TABLE 1

| Cutaneous Absorption Parameter (0.5 mg/25 μl/10 cm$^2$/body. n = 5, mean ± S. E.) | | | |
|---|---|---|---|
| | $C_{max}$ (ng/ml) | $T_{max}$ (hr) | $AUC_{0-24}$ (ng · hr/ml) |
| Ethanol only (control) | n.d. | — | — |
| Example 1 | 18.932 ± 0.972 | 17.6 ± 3.9 | 312.433 ± 19.676 |
| Example 3 | 6.786 ± 0.865 | 8.0 ± 0.0 | 114.167 ± 14.731 |
| Example 5 | 28.974 ± 3.831 | 24.0 ± 0.0 | 413.313 ± 59.002 |

As seen from the table 1, it is clear that the lotion of the present invention is excellent in absorption and provides sustained release.

The lotion of the present invention is stable and excellent in absorption and provides sustained release. Also, the lotion of the present invention has less irritation against the skin.

In view of the pharmacological activities of the tricyclic compound (I), the lotion of the present invention is useful for the treatment and/or prophylaxis of inflammatory and hyperproliferative skin diseases and cutaneous manifestations of immunologically-mediated illnesses, such as psoriasis, atopical dermatitis, contact dermatitis and further eczematous dermatitises, seborrhoeis dermatitis, lichen planus, pemphigus, bullous pemphigoid, epidermolysis bullosa, urticaria, angioedemas, vasculitides, erythemas, cutaneous eosinophilias, lupus erythematosus, alopecia areata, and the like; male pattern alopecia or alopecia senilis; skin diseases such as dermatomyositis, leukoderma vulgaris, ichthyosis vulgaris, photoallergic sensitivity, cutaneous T cell lymphoma, acne, various types of autoimmune diseases (chronic rheumatoid arthritis, scleroderma, etc.) and the like.

We claim:

1. A lotion comprising FK506, represented by the following formula:

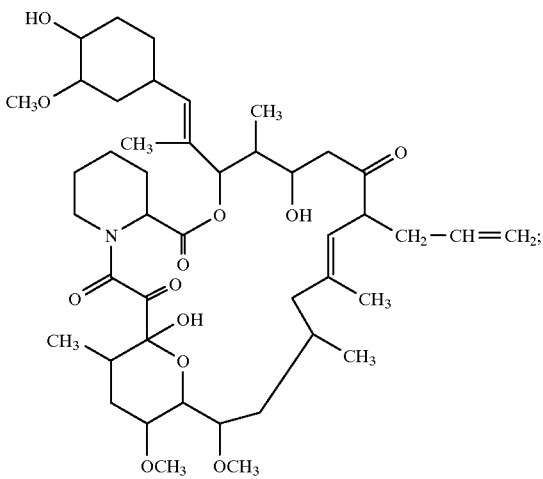

a solubilizing and/or absorption-promoting agent selected from the group consisting of diisopropyl adipate, diethyl sebacate and isopropyl myristate; a water-miscible liquid medium; and optionally an emulsifier and/or a viscosity increasing agent, wherein said FK506 is dissolved or dispersed finely and uniformly in said liquid medium.

2. A lotion as claimed in claim 1 in which the FK506 is contained in the lotion in an amount of 0.01 to 10% (w/w).

3. A lotion as claimed in claim 1, in which the solubilizing and/or absorption-promoting agent is contained in the lotion in an amount of 1 to 30% (w/w).

4. A lotion as claimed in claim 1 in which the liquid medium is water, a lower alcohol, glycerin, a glycol or a mixture thereof.

5. A lotion as claimed in claim 4 in which the liquid medium is a lower alcohol.

6. A lotion as claimed in claim 5 in which the lower alcohol is ethanol.

7. A lotion as claimed in claim 4 in which the liquid medium is a mixture of water and ethanol.

8. A lotion as claimed in claim 1 in which the emulsifier is a natural emulsifier selected from the group consisting of yolk lecithin, soybean lecithin or hydrogenated substance thereof, phosphatidylcholine, phosphatidylserine, sphingomyelin, gum arabic and gelatin, or a synthetic emulsifier selected from the group consisting of cationic, anionic and nonionic surface active agents.

9. A lotion as claimed in claim 8 in which the emulsifier is a polyoxyethylene hardened castor oil surface active agent.

10. A lotion as claimed in claim 1 is which the viscosity increasing agent is carboxypolymethylene.

11. A lotion as claimed in claim 1 in which solubilizing and/or absorption-promoting agent is diisopropyl adipate.

12. A lotion as claimed in claim 1 in which solubilizing and/or absorption-promoting agent is diethyl sebacate.

13. A lotion as claimed in claim 1 in which solubilizing and/or absorption-promoting agent is isopropyl myristate.

* * * * *